United States Patent [19]

Millan

[11] Patent Number: 5,081,227

[45] Date of Patent: Jan. 14, 1992

[54] GERM CELL ALKALINE PHOSPHATASE

[75] Inventor: Jose L. Millan, San Diego, Calif.

[73] Assignee: La Jolla Cancer Research Foundation, La Jolla, Calif.

[21] Appl. No.: 164,138

[22] Filed: Mar. 4, 1988

[51] Int. Cl.$^5$ .............................. C07K 7/06; C07K 7/10
[52] U.S. Cl. ............................ 530/328; 530/300; 530/329; 530/350; 530/403; 530/806; 435/21; 435/195
[58] Field of Search ............... 435/21, 172.1; 530/350, 530/403, 412, 806, 808, 828, 850, 328, 329, 300

[56] References Cited

U.S. PATENT DOCUMENTS 4,375,514  3/1983  Siewert et al. .................. 435/172.1

OTHER PUBLICATIONS

Watanabe et al., J. of Biol. Chem., vol. 264, No. 21, Jul. 25, 1989, pp. 12611–12619.
Millan et al., Proc. Nat. Acad. Sci, vol. 85, May 1988 (Developmental Biology), pp. 3024–3028.
Millan, Jose; Nustad, Kjell; Norgaard-Pedersen, 1985, Highly Sensitive Solid-Phase Immunoenzymometric Assay for Placental and Placental-Like Alkaline Phosphatases with a Monoclonal Antibody and Monodisperse Polymer Particles, Clinical Chemistry, 31:1:54–59.
Millan, Jose; Stigbrand, Torgny, 1983, Antigenic Determinants of Human Placental and Testicular Placental—Like Alkaline Phosphatases as Mapped by Monoclonal Antibodies, Eur. J. Biochem. 136: 1–7.
Shameem, G. et al., Clin. Chem. 33, No. 2: 248–252 (1987).
Wei, S. et al., Eur. J. Biochem., 118:39–45 (1981).
Millan, Jose, Jour. Biol. Chem., 261, No. 7:3112–3115 (1986).

Primary Examiner—Sam Rosen
Attorney, Agent, or Firm—Pretty Schroeder Brueggemann & Clark

[57] ABSTRACT

The invention relates to structural and regulatory DNA sequences encoding the germ cell ALP gene. These sequences differ at identified positions from the PLAP gene. Labelled nucleotide sequences complementary to germ cell ALP encoding nucleotide sequences but differing from PLAP may be used to detect the presence of the gene. The invention also relates to gene fragments specifying amino acid sequences which are specific to germ cell ALP and to antibodies raised against germ cell ALP-specific peptide fragments, their diagnostic and therapeutic uses.

3 Claims, 4 Drawing Sheets

```
CCCGGGCTGTGTGCTTCCAGCCTCCCCTCTCGACACCAGAACAGAGCCTGGCCCCCAGCTCCCAGGAAATACAGAAAAAAAAATGGTGATGAACGAGTGACAGGGTGTGTCTTGTTC   120

CACACAAGAGACACAGTGAGCAGGGGTTGGGGAGGGCCCCTGGGCAGGATGCACACTGCACTATACCCAAATCCCACCCTTCCCTGGGACACCTGGTCACCCTAAGCTGCCTTTC    240
                      Sp1
TCAGGACCCAGCCCAGCCCAGCCCAACCCTGCCACTCCCTTCAGCCAGTGTGGCTTCAGTGTCAAGAGGCTGGGCGGGGTCAAGGTGGTAACAAGGGGAGGGGCCAGGACACAGTT   360
     TATA Box                                                                                                Exon I
TTCCCTGATTTAAACCCAGGCAGCCTGGAGTGCAGCTCATATCCCATCTGGGATTTCCGCCTCGCCGTCTCCGACTGCTTCCAGACATGCAGGGGCCCTGGTGCTGCTCCTGCTGG   480
                                                                               MetGlnGlyProTrpValLeuLeuLeuLeuG
                                                                                                  Leu    CysMet    (LeuLeuLeu)
GCCTGAGGCTACAGCTCTCCCTGGCATCATCCCAGTAATGAGGCTCCCAGCCTGCCTACACACACACACACACACACACACCCCCAGCCCCAGCCCCAGCCTGACCTGACCTTTGCTCTCC   600
lyLeuArgLeuGlnLeuSerLeuGlyIleIleProV                                                         Exon II
GCCTGGCCAGTTGAGGAGGAGAACCCGGACTTCTGGAACCCAGGCAGCCGAGGCCCTGGGTGCGCCAGCCTGCACAGAACCTCATCATGTTCCTG   720
alGluGlyAsnProAspPheTrpAsnArgGlnAlaAlaGluAlaLysLeuGlnProAlaGlnThrAlaAlaLysAsnLeuIleMetPheLeu
        Glu                                                                               Ile
CCCTGGCCAGTTGAGGAGGAGAACCCGGACTTCTGGAACCCAGGCAGCCGAGGCCCTGGGTGCGCCAGCCTGCACAGAACCTCATCATGTTCCTG GGTGACGGTGAGTGAGCCAGCCTTCCAGCCCCGACCCTCAGTGGTTCCAGGACCAAGCCTGGGAGCAGCCCTGGGGACCCCGGGAGGCCCTCAGGG   840
GlyAspG                                                                                          ly
                                                                                                 Exon III
ATGGGGGTGTCTACGGTGACAGTGCCAGGATCCTAAAAGGGCAGAAGAAGGACAAACTGGGGCCTCCTGGCCATGACCGCTTCCGTGGCTGGTCGTCCAAGGTAAGT   960
MetGlyValSerThrValThrAlaAlaArgIleLeuLysGlyGlnLysLysAspLysLeuGlyProGluThrPheLeuAlaMetAspArgPheProTyrValAlaLeuSerLys
                                                                                  IlePro
GCTGGGGTACCCTTAGAGTCCTCCAAGCAGAGAAGGGGAATCCTGGCTATGGAGGTGTGTAGGAGGGACCCCTAAACAGCTGGGGCTCCAATAAGAGCTGGAGGCAGTTGGAATCCC  1080
                                                                                                   Exon IV
AGAGGACAGAGATCAGGGTCTTGTTTGTCTGCCCAGAGAAGAGCTCAGAGTGTCTCTGTCCCAGACATACAGTGCCAGACAAGCATGTGCCAGACAGTGAGCCACAGCCACGGCCTAC  1200
                                                              ThrTyrSerValAspLysHisValProAspSerGlyAlaThrAlaThrAlaTyr
                                                                   Asn
CTGTGCGGGGTCAAGGGCAACTTCCAGACATTGGTTGAGTGCAGCCCCGCCGCCTTTAACCAGTGCAACGACGACGCGGCAACGAGGTCATCTCCGTGTGAATCGGGCAAGAAAGCA  1320
LeuCysGlyValLysGlyAsnPheGlnThrIleGlyLeuSerAlaAlaAlaArgPheAsnGlnCysAsnThrThrArgGlyAsnGluValIleSerValValAsnArgAlaLysAlaAla
                                                                                                  Met
GGTGGAGCTGGGCCCGGCTGTGGGGTCAGGGCCAGAGCCCAGTGGCAGAAAGTCAGTGGGAGTGGTAACCACCACACGGGTGCAGCATG   1440
                                                     lyLysSerValGlyValValThrThrThrArgValGlnHisA
G
```

FIG. 2-1

```
CCTCGCAGCCGGCACCTACGCCCACCTGAACCCAACTGGTACTCGGATGCCGAGGACATGCCACCAGCTCATCTCCAACA    1560
laSerProAlaGlyThrTyrAlaHisThrValAsnArgAsnTrpTyrSerAspValProAlaSerAlaArgGlnGluGlyCysGlnAspIleAlaThrGlnLeuIleSerAsnM

TGGACATTGATGTGCGACCCCGGGCCAAGGGTGGGGCTGGGCAGGAGTAGCAGGGGCACCAGCAGCAACCAAAAGCCTTATCTGGGCCAGCAGGGTCTGGAAGGT            1680
etAspIleAsp

GGGGTTGGGGGCGTAGAAGGCGCACCAGGCTGGGCCATTCCCACAGCCTTGGGGAGGGAGTCAGGGGCTCTGCATGAGGAGGGACACGGGCCTAGCCATGGCCCAAAGTCCACCTGC    1800
                                                                Exon VI CCCATCCTCTGTTCCCAGGTGATCCTAGGTGGAGGCCGAAAGTACATGTTTCCCATGGGACCCTGAGTACCAGATGACTACAGCCAAGGTGGGACCAGGCTGGACGGGAAG          1920
                                    ValIleLeuGlyGlyGlyTyrMetPheProMetGlyThrProAspTyrSerGlnGlyThrProAspGlyLys AATCTGGTGCAGGAATGGCTGGCGAAGCACCAGGTGATGGGGGCTGGTGGTGCTGGGCACACAGCAGGGGAGAGGTGTGGGGGCTCTGAGGCCTGGCTCTCT                    2040
                            ValIleLeuGlyGlyGlyTyrMetPheProMetGlyThrProAspTyrSerGlnGlyThrProAspGlyLys       Exon VII AATCTGGTGCAGGAATGGCTGGCGAAGCACCAGGTGATGGGGGCTGGTGGTGCTGGGCACACAGCAGGGGAGAGGTGTGGGGGCTCTGAGGCCTGGCTCTCT                    2040
AsnLeuValGlnGluTrpLeuAlaLysHisGln                                    Exon VII CCCTCCCCCGCAGGGTGCCCGGTACGTGTGGAACCCACTGAGCTCCTGCAGGCTTCCTGAACCGTCTGTGACCCATCTCATGGGTAATGACCCCCTTCTGCCCTGGCATCCTCAGAT    2160
            GlyAlaArgTyrValTrpAsnArgThrGluLeuLeuGlnAlaSerLeuAspArgSerValThrHisLeuMetG
                Arg GGCCTCAGATGCCACTTCTGAGCCTGTGTGCACATCCGCCAGCACCCCTTGTCCCACAGGTCTCTTTGAGCCTGGAGACATGAAAT                                    2280
            Exon VIII                                            lyLeuPheGluProGlyAspMetLysT ACGAGATCCACCGAGACTCCACACTGGACCCCTCCCTGATGGAGATGACAGAGGCTGCCCTGCCTGAGCAGGAGAACCCCCGGCTTCTTCCTCTTCGTGGAGGGTGCGTGGTGGC    2400
yrGluIleHisArgAspSerThrLeuAspProSerLeuMetGluMetThrGluAlaLeuLeuLeuSerArgAsnProArgGlyPhePheLeuPheValGluG
                                                                Arg CCTGGGAGTTGGGGGGTTGGAGCAGGAGCAGGCTCAGATCTCCCCCTTCCTGCAGTGGTCAGCCATGACCATGGTCATCATGACCATCGACAAGGCTCATGAAAGCAGGGCTTACCGGGCACTGA    2520
                        lyGlyArgIleAspHisGlyHisHisGlyHisSerArgAlaTyrArgAlaLeuT CTGAGACGATCATGTTCGACGACGCATTGAGAGGGCGGCAGGCTCACCAGGGAGGAGGACACGCCAGTGCCCACCACTGCCGACCACTCTTCCTTCCGGAGGTACCCCC            2640
hrGluThrIleMetPheAspAspAlaIleLeuArgAlaGlyGlnLeuThrSerLeuValThrAlaAspHisSerPheGlyGlyTyrProL TGGCAGGGAGCCTCCATCTTCGGTAGGCCTGGGGATGAGTGGCCAGGTGCTGCTGCAGGCAATTAAGTGGGTGAAATCTGAGCCTCAGTCTCCTCGTCAAGTGGGAGTAATGCTGGCAC    2760
euArgGlySerSerIlePheG CAGCCTAATAGGTCCTCTCTGCGGACTAAGCCCCTGACCAGGCAAAACGTGCGGTGCCTAGCACGTGGGAGACACTCCACAGCTGTGTTCAGCTCAACACCAGGGACCCCTCTCTGCAG      2880
```

FIG. 2-2

```
                                                                                           Exon X
GGCTGGCCCTGGCAAGGCCCGGGACAGGAAGGCCTACACGGTTCCAGGCTATGTGTCCAGGCTACACGGAAACGGTCCAGGCTACACGGAGACGGGCCCCGGCCCCGGATGTTACGGAGAGCGAGAGCGGTG           3000
  yLeuAlaProGlyLysAlaArgAspArgLysAlaTyrThrValLeuLeuTyrValGlyAsnGlyTyrValLeuLysLysAspGlyAlaArgProAspValThrGluSerGluSerG
                                                                                                                            1
AGTGCCGTGGGGTGGCCTGAGGGGACCAGGGTGCCAAGGATGGGGGAAGGGTCACCTCTTGTCTGCCTGAACTTCCTACTGAACTGAAACTTCCAACCAGG                                      3120
                                          Exon XI
GAGCCCCGAGTATCGGCAGCAGTCAGCAGGTGCCCCTGACGAGTAGTGCCCCTGACGAGGAGACCCACGCAGGAGGACGTGGCGGCGTGTTCGCGCGGCCCCCAGGGCACTGGTTCACGGGCGTGCAGGAGCA       3240
  ySerProGlyTyrArgGlnGlnSerAlaValProLeuAspSerAlaValAlaValAlaGlyGluAspValAlaValPheAlaAlaArgGlyProGlnAlaHisLeuValHisGlyValGlnGluG
                                                                                                                  lu
GACCTTCATAGGCACGTCATGGCCTTCGCGCGCTGCCTGGAGCCCTGCCTGGAGCCCTGACCCGCGACCGCCGGGGCGCCACCACGACCGCCGGGGCGCCACCGACCGCCGTGCCGTGGTCCCGC             3360
  nThrPhelleAlaHisValMetAlaPheAlaPheAlaAlaCysAspLeuAlaProTyrThrAlaAspAlaAlaHisProGlyProSerValProAl
                                                                                            Arg
GTGCTTCCTCTGCTGCAGGGACCTTGCTGCTGCTGGGGACGGCCACTGCTCCCGTGAGTGTCCCGTGCCCTGCTCCCACCTCCAG                                                     3480
  aLeuLeuProLeuLeuAlaGlyThrLeuLeuLeuLeuGlyLeuThrAlaThrAlaProEnd
TTCTGCTGCCGGACCTCCACCTGGAGCTGTCACCCCCGGAGTCGCCACACAGACTGTCCTGCCATGGAACCTTCCCTCCCGGTGCACCCTGGGGACCGAGCCCTTGACACCACGCCCTT                  3600
TGCTTTATCTTGCTCTTAAATTTTGGCCCACTCCAGGACTGGGATTTGTGCCTGGCAGCTGCCTGCATTTCAGGAAAAGAGGAGGCTCAGACCATCAGCCCCGCCATATCCT                         3720
GAGGTGGATCAGGCAGGCTCTCTCCCCGGGACATGAGGCACCCATACCTAGGACCCCCTGCGCCTTTTAGCTTCAGTCATGCAGCACCTGAGGGACACAAGGACTGGGTGCATCA                      3840
GGACGCCTTGGAGAGCCGTGGCTTCCTGCCACCCTGCAACCCAGCCAAGGAGCTGCTGGTGGGGATCCCCAGGGCTTTGACACAGTCCTCTGCTCCCTCCACTGGG                               3960
CTAATTCTACACCCCTGTGCCCCTCCTAGGCGCATGAGTCAGAGAGTCCAGATGGCCAAGTCACACCACTCAGAGTGTTCGACGCCCTAAGGTCCTCATTCCAGCACCACCTGAGTTCCGAGGA            4080
GCACCTGGGAAGCTCTGGGTGCAGATAGCAGTCCAGAGTCCATGCCCCGCTAGGCCATCTGGGTGCTGGGCATGGATTTCTCAGCAAGGAAGACTCATTACCTTCCTCCCTGGGCCT                   4200
CCATTCTTCTGGGAAACACAAAGCAATAATAAAAGGAAGTGTTAGACAATGTAATGCCAGTACTACTTCCTAGCATAAAAATCATGACTGAATGTGACACAGTGGCTGAGGGGGTGGAT                 4320
AACACAGGCCAGGAGGGCTGCTGAGGAGCAGATGACTGAGCAGGAGATGACTGAGCAGGAGAGCGCTGAGCAAGGTGCACAGCAAGGTGGAGCAGCACAAAGGCCCTGAGCAAGGTGGAGCAGCAGCAGCACAAAGGCCCTGGGAGTGTCAGCAGGCTGTC  4440
TGGGAGGCCAGGGGTGGATCAGAGGGTGGGTAGATGGGGTAAAGCTT                                                                                         4487
```

FIG. 2-3

GERM CELL ALKALINE PHOSPHATASE

The invention relates to the field of oncotrophoblast genes, and more specifically to alkaline phosphatase genes and materials produced therefrom.

Human alkaline phosphatases (ALP) comprise a family of functionally related enzymes generally identified by the tissues in which they appear. Placental ALP (PLAP) has received considerable attention since the discovery that the enzyme, which is normally expressed in significant amounts only in the placenta, may be found in certain tumors, thus providing a potential marker for such cancer. Subsequently, a PLAP-like isozyme, termed the "Nagao isozyme," was found to be expressed in certain lung cancers and germ cell tumors of the testis, particularly seminomas, for which it is a useful marker. The term "germ cell ALP" will be used herein when referring to the PLAP-like Nagao isozyme since germ cells are the predominant cell type where normal expression has been observed.

The recent cloning of cDNAs has resulted in the identification of three distinct genes coding for PLAP, liver-bone-kidney type ALP and intestinal ALP. The PLAP locus has high variability, the enzyme exhibiting the highest degree of polymorphism of any human enzyme as determined by electrophoretic and immunochemical techniques. While the Nagao isozyme has been suspected of representing a slower-migrating allelic variant of PLAP, the question of identity between PLAP and Nagao isozyme has remained unresolved. Studies using allotype specific polyclonal and monoclonal antibodies against PLAP allelic variants have allowed the detection of structural differences in the Nagao isozyme that led to the the proposal that a distinct gene locus is responsible for the expression of this enzyme.

Serological measurements of PLAP and germ cell ALP levels are of clinical value in the evaluation of patients with testicular, ovarian, and certain other cancers. Both isozymes are potentially useful targets for the immunolocalization of primary and metastatic tumors by using radiolabelled monoclonal antibodies. Thus far, however, the monoclonal and polyclonal reagents available for the clinical monitoring of these markers cross react with both PLAP and germ cell ALP. The unavailablity of purified germ cell ALP or, more particularly, germ cell ALP fragments of unique sequence, has prevented the development of highly desirable specific reagents. Thus, it has not been possible to develop antibodies specific for this ALP variant.

There thus exists a need for means to accurately determine the presence of germ cell ALP. Such means would preferably be based on monoclonal or monospecific polyclonal antibodies raised against peptide sequences specific to germ cell ALP. The present invention satisfies this need and provides related advantages as well.

SUMMARY OF THE INVENTION

The invention relates to the DNA sequences encoding mammalian germ cell ALP. The determination of the structure of the germ cell ALP gene provides means of accurately determining the presence of germ cell ALP and of discriminating between germ cell ALP and other alkaline phosphatases.

Thus, in one aspect, the invention relates to structural and regulatory DNA sequences encoding the germ cell ALP gene. These sequences differ at identified positions from the PLAP gene. Labelled nucleotide sequences complementary to germ cell ALP encoding nucleotide sequences but differing from PLAP may be used to detect the presence of the gene. In another aspect, the invention relates to gene fragments specifying amino acid sequences which are specific to germ cell ALP. The invention further relates to antibodies raised against germ cell ALP-specific peptide fragments, their diagnostic and therapeutic uses.

BRIEF DESCRIPTION OF THE DRAWINGS

FIG. 2 shows a restriction enzyme map of the germ cell ALP gene.

DETAILED DESCRIPTION OF THE INVENTION

A. Definitions

Figure 1:
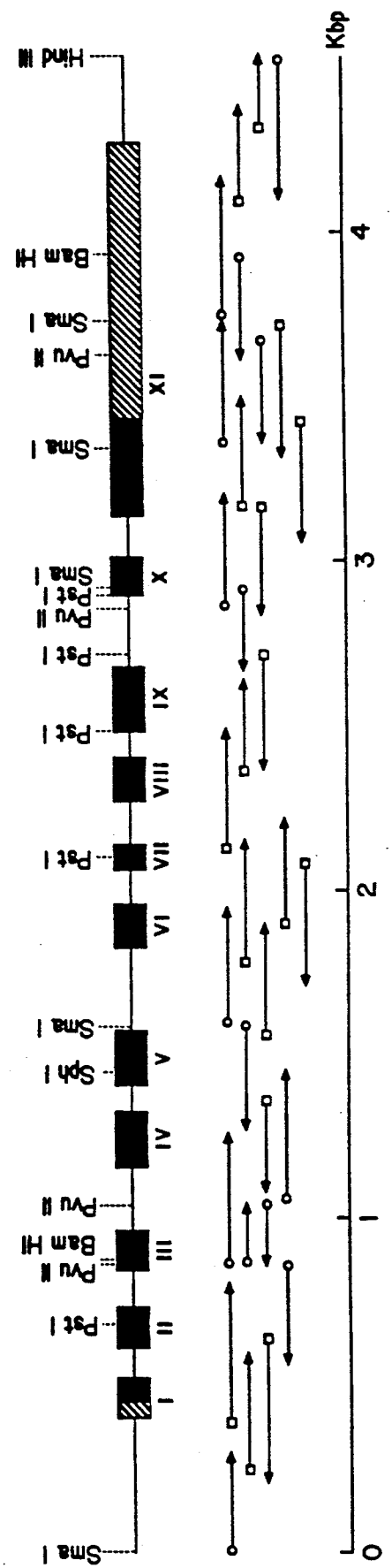
FIG. 1 shows the DNA sequence encoding germ cell ALP and the corresponding amino acid sequence of germ cell ALP. Those residues that are different in the PLAP gene are indicated immediately under the substituted position.

As used herein, "germ cell ALP" refers to an enzyme having alkaline phosphatase activity which is normally present in small amounts in the testis and the thymus and is expressed in germ cell tumors of the testis, particularly seminomas. It is synonymous with "Nagao Isozyme" and is distinguished from PLAP by its slower migration on starch gels and its greater sensitivity to the non-competitive inhibitor L-leucine. The term germ cell ALP refers both to the native amino acid sequences and to minor modifications thereof. It is understood that limited modifications may be made without affecting the activity of the enzyme.

The term "DNA sequence which codes for germ cell ALP" as used herein refers to the primary nucleotide sequence of a gene encoding the amino acid sequence of germ cell ALP, as defined above. The sequence of the human gene is presented in FIG. 1. The gene may or may not be expressed in the native host. The term refers both to the precise nucleotide sequence of a gene found in a mammalian host as well as modified genes which still code for germ cell ALP. Certain differences in nucleotide sequences may exist between individual organisms, which are called alleles. Such allelic differences may or may not result in differences in amino acid sequence of the encoded peptide while still encoding an enzyme having germ cell ALP activity.

Basic techniques for preparing DNA libraries and oligonucleotide probes, as well as their screening by nucleic acid hybridization, are well known to those of ordinary skill in the art. See, e.g., DNA CLONING: VOLUME I (D. M. Glover ed. 1985); NUCLEIC ACID HYBRIDIZATION (B. D. Hames and S. J. Higgins eds. 1985); OLIGONUCLEOTIDE SYNTHESIS (M. J. Gate ed. 1984); T. Maniatis, E. F. Frisch & J. Sambrook, MOLECULAR CLONING: A LABORATORY MANUAL (1982).

First, a DNA library is prepared. The library can consist of a genomic DNA library from a selected mammal, such as a human. Human genomic libraries are known in the art. See, e.g., Lawn et al., (1978) Cell 15:1157–1174. DNA libraries can also be constructed of cDNA prepared from a poly-A RNA (mRNA) fraction by reverse transcription. See, e.g., U.S. Pat. Nos. 4,446,235; 4,440,859; 4,433,140; 4,431,740; 4,370,417 and 4,363,877. The mRNA is isolated from an appropriate cell line or tissue known to express the gene. cDNA (or genomic DNA is cloned into a vector suitable for construction of a library. A preferred vector is a bacteriophage vector, such as phage lambda. The construction of an appropriate library is within the skill of the art.

Once the library is constructed, either oligonucleotides or cDNA or riboprobes derived from the cDNA can be used to probe the library and isolate the desired gene. The oligonucleotides are synthesized by any appropriate method, such as by the use of an automated DNA synthesizer. The particular nucleotide sequences selected are chosen so as to correspond to the codons encoding a known amino acid sequence from the protein. Since the genetic code is redundant, it will often be necessary to synthesize several oligonucleotides to cover all, or a reasonable number, of the possible nucleotide sequences which encode a particular region of the protein. Thus, it is generally preferred in selecting a region upon which to base the probes, that the region not contain amino acids whose codons are highly degenerate. In certain circumstances, one of skill in the art may find it desirable to prepare probes that are fairly long, and/or encompass regions of the amino acid sequence which would have a high degree of redundancy in corresponding nucleic acid sequences, particularly if this lengthy and/or redundant region is highly characteristic of the protein. Probes covering the complete gene, or a substantial part of the genome, may also be appropriate, depending upon the expected degree of homology. It may also be desirable to use two probes, or sets of probes, each to different regions of the gene, in a single hybridization experiment. Automated oligonucleotide synthesis has made the preparation of large families of probes relatively straightforward. While the exact length of the probe employed is not critical, generally it is recognized in the art that probes from about 14 to about 20 bases are usually effective. Longer probes of about 25 to about 60 bases are also used.

The selected oligonucleotide probes are labeled with a marker, such as a radionucleotide or biotin, using standard procedures. The labeled set of probes is then used in the screening step, which consists of allowing the single-stranded probe to hybridize to isolated denatured DNA from the library, according to standard techniques. Either stringent or permissive hybridization conditions could be appropriate, depending upon several factors, such as the length of the probe and whether the probes are derived from the same species as the library, or an evolutionarily close or distant species. The selection of the appropriate conditions is within the skill of the art. See generally, NUCLEIC ACID HYBRIDIZATION, sucra. The basic requirement is that hybridization conditions be of sufficient stringency so that selective hybridization occurs; i.e., hybridization is due to a sufficient degree of nucleic acid homology (e.g., at least about 75%), as opposed to nonspecific binding. Once a clone from the screened library has been identified by positive hybridization, it can be confirmed by restriction enzyme analysis and DNA sequencing that the particular library insert contains the desired gene.

Alternatively, a DNA coding sequence for the desired protein can be prepared synthetically from overlapping oligonucleotides whose sequence contains codons for the amino acid sequence of the protein. Such oligonucleotides are prepared by standard methods and assembled into a complete coding sequence. See, e.g., Edge, (1981) Nature 292:756; Nambair et al., (1984) Science 223:1299; Jay et al., (1984) J. Biol. Chem. 259:6311.

A DNA molecule containing the coding sequence for the protein can be cloned in any suitable vector and thereby obtaining a single cloned species of DNA. Numerous cloning vectors are known to those of skill in the art, and the selection of an appropriate cloning vector is a matter of choice. Examples of recombinant DNA vectors for cloning and the host cells which they transform include bacteriophage (*E.coli*), λgt11, λgt10, charon 28, charon 4A, EMBL 3 or EMBL 4 pBR322 (*E.coli*), pACYC177 (*E.coli*), pKT230 (gram-negative bacteria, pGV1106 (gram-negative bacteria), pLAFR1 (gram-negative bacteria), pME290 (non-*E.coli* gram-negative bacteria), pHV14 (*E.coli* and *Bacillus subtilis*), pBD9 (Bacillus), pIJ61 (Strectomyces), pUC6 (Streptomyces), actinophage C31 (Streptomyces), YIp5 (yeast), YCp19 (yeast), and bovine papilloma virus (mammalian cells). See generally, DNA CLONING: VOLUMES I & II, supra; MOLECULAR CLONING: A LABORATORY MANUAL, supra.

In one embodiment of the present invention, the coding sequence of the germ cell ALP gene is placed under the control of a promoter, ribosome binding site (for bacterial expression) and, optionally, an operator (collectively referred to herein as "control" sequences), so that the DNA sequence encoding the protein (referred to herein as the "coding" sequence) is transcribed into RNA in the host cell transformed by the vector. The coding sequence may or may not contain a signal peptide or leader sequence. The determination of the point at which the mature protein begins and the signal peptide ends is easily determined from the N-terminal amino acid sequence of the mature protein. The protein can also be expressed in the form of a fusion protein, wherein a heterologous amino acid sequence is expressed at the N-terminal. See, e.g., U.S. Pat. Nos. 4,431,739; 4,425,437.

The recombinant vector is constructed so that the germ cell ALP protein coding sequence is located in the vector with the appropriate control sequences, the positioning and orientation of the germ cell ALP protein coding sequence with respect to the control sequences being such that the coding sequence is transcribed under the control of the control sequences (i.e., by RNA polymerase which attaches to the DNA molecule at the control sequences). The control sequences may be ligated to the coding sequence prior to insertion into a vector, such as the cloning vectors described above. Alternatively, the coding sequence can be cloned directly into an expression vector which already contains the control sequence and an appropriate restriction site downstream from control sequences. For expression of the germ cell ALP protein coding sequence in procaryotes and yeast, the control sequences will be heterologous to the coding sequence. If the host cell is a procaryote, it is also necessary that the coding sequence be free of introns; e.g., cDNA. If the selected host cell is a mammalian cell, the control sequences can be heterologous or homologous to the germ cell ALP protein coding sequence, and the coding sequence can be genomic DNA containing introns or cDNA. Either genomic or cDNA coding sequence may be expressed in yeast.

A number of procaryotic expression vectors are known in the art. See, e.g., U.S. Pat. Nos. 4,440,859; 4,436,815; 4,431,740; 4,431,739; 4,428,941; 4,425,437; 4,418,149; 4,411,994; 4,366,246; 4,342,832. See also British Patent Specifications GB 2,121,054; GB 2,008,123; GB 2,007,675; and European Patent Specification 103,395. Preferred expression vectors, however, are those for use in eucaryotic systems. Yeast expression vectors are known in the art. See, e.g., U.S. Pat. Nos. 4,446,235; 4,443,539; 4,430,428. See also European Patent Specifications 103,409; 100,561; 96,491.

Recombinant germ cell ALP protein can be produced by growing host cells transformed by the expression vector described above under conditions whereby the germ cell ALP protein is produced. The germ cell ALP protein is then isolated from the host cells and purified. If the expression system secretes germ cell ALP protein into growth media, the protein can be purified directly from cell-free media. If the protein is not secreted, it is isolated from cell lysates. The selection of the appropriate growth conditions and recovery methods are within the skill of the art. Recombinant germ cell ALP protein may be unglycosylated or have a different glycosylation pattern than the native molecule depending upon the host that is used to produce it.

Two different human genomic DNA libraries, one derived from placental tissue and one from spleen tissue, were screened for the presence of PLAP-related sequences. Restriction enzyme analysis and hybridization after Southern blotting revealed a number of related clones, one which was present in both libraries being chosen for further study. Hybridization with subfragments of the PLAP cDNA indicated that the chosen clone contained sequences that spanned the entire PLAP cDNA. The sequence of the gene from the chosen clone, which is presented in FIG. 1, indicates that it encodes a protein highly homologous, but different from PLAP. The protein encoded by the gene is germ cell ALP.

The sequence of the cDNA coding for PLAP has been previously described (Millan, J. L. (1986) J. Biol. Chem. 261:3112). The intron-exon junctions of the germ cell ALP gene were identified by aligning its genomic sequences with the sequence of the PLAP cDNA. The germ cell ALP gene is interrupted by ten small introns ranging in size from 76 basepairs (bp) (intron IV) to 427 bp (intron V). The exons are small and of comparable size (73 bp to 312 bp) with the exception of exon XI (800 bp) that encodes the carboxy terminus of the protein and also includes the entire 3' untranslated region of the cDNA. The intron-exon structure and restriction enzyme map of the germ cell ALP gene, as well as the sequencing strategy, are presented in FIG. 2.

The deduced amino acid sequence of the germ cell ALP is presented in FIG. 1. The mature germ cell ALP is composed, as is PLAP, of 513 amino acids. The homology between these two gene products is 98%; twelve amino acid mutations are scattered throughout the germ cell ALP molecule. Those amino acids that differ in the PLAP sequence are indicated immediately underneath the germ cell ALP residues.

In spite of the high degree of sequence conservation between PLAP and germ cell ALP, the restriction enzyme maps of these two genes are considerably different. Major differences between germ cell ALP and PLAP are found in exon I. The 5' untranslated region immediately upstream of the start codon for translation is different from the corresponding PLAP cDNA sequence. The signal peptide sequence of the germ cell ALP is different from the PLAP signal peptide at positions +1, +4, and 5 and shows deletions of three leucines with respect to PLAP.

Either native or synthetic germ cell ALP protein can be used to produce antibodies, either polyclonal or monoclonal. If polyclonal antibodies are desired, purified germ cell ALP protein is used to immunize a selected mammal (e.g., mouse, rabbit, goat, horse, etc.) and serum from the immunized animal is later collected and treated according to known procedures. Antisera containing polyclonal antibodies to a variety of antigens in addition to the germ cell ALP protein can be made substantially free of antibodies which are not anti-germ cell ALP specific by passing the composition through a column to which non-germ cell ALP protein has been bound. After washing, antibodies to the non-germ cell ALP proteins will bind to the column, whereas anti-germ line ALP antibodies elute in the flow through. Monoclonal anti-germ cell ALP protein antibodies can also be readily produced by one skilled in the art. The general methodology for making monoclonal antibodies by fusing myelomas and lymphocytes to form hybridomas is well known. Such cells are screened to determine whether they secrete the desired antibodies, and can then be grown either in culture or in the peritoneal cavity of a mammal. Antibodies can be recovered from the supernatent or ascites fluid. Immortal, antibody producing cell lines can also be created by techniques other than fusion, such as direct transformation of B lymphocytes with oncogenic DNA, or transfection with Epstein-Barr virus. See, e.g.. M. Schreier et al., HYBRIDOMA TECHNIQUES (1980); Hammerling et al., MONOCLONAL ANTIBODIES AND T-CELL HYBRIDOMAS (1981); Kennett et al., MONOCLONAL ANTIBODIES (1980).

By employing germ cell ALP protein (native or synthetic) as an antigen in the immunization of the source of the B-cells immortalized for the production of monoclonal antibodies, a panel of monoclonal antibodies recognizing epitopes at different sites on the germ cell ALP protein molecule can be obtained. Antibodies which recognize a site on the germ cell ALP protein are useful, for example, in the purification of the protein from cell lysates or fermentation media, in characterization of the protein and in identifying immunologically related proteins. In general, as is known in the art, the anti-germ cell ALP protein antibody is fixed (immobilized) to a solid support, such as a column or latex beads, contacted with a solution containing the germ cell ALP protein, and separated from the solution. The germ cell ALP protein, bound to the immobilized antibodies, is then eluted.

Antisera specific to the germ cell ALP were generated by immunizing with a synthetic peptide derived from the amino acid sequence deduced from the nucleotide sequence of the germ cell ALP gene. Preferably, the synthetic peptide is chosen so as to incorporate known amino acid differences from PLAP. Two amino acid mutations with respect to PLAP are clustered in exon III of the germ cell ALP sequence. The synthetic nonamer NH$_2$-Lys-Leu-Gly-Pro-Glu-Thr-Phe-Leu-Ala-COOH includes both substitutions, as underlined, and was thus chosen as the immunogen. Other synthetic peptides incorporating the known amino acid substitutions can also be used.

The synthetic peptide immunogen was injected into a rabbit although other mammals could be used as well. The antiserum was collected and affinity purified according to methods well known in the art. Antisera thus raised against the nonamer described above was found to react well with germ cell ALP but not to recognize PLAP.

Alternatively, monoclonal antibodies specific to germ cell ALP can be generated using germ cell ALP-specific synthetic peptide fragments as immunogens. Lymphocytes recovered from the immunized animals can then be fused with immortal cells according to methods well-known in the art in order to form hybridomas capable of producing germ cell ALP specific monoclonal antibodies.

Antibodies specific to germ cell ALP have a number of diagnostic uses. For example, they may be employed in an immunoassay to detect the presence of germ cell ALP. Various appropriate immunoassay formats are well known to those skilled in the art. Additionally, such antibodies may be labeled with a detectable label and used to target and image tissue containing germ cell ALP. Alternatively, antibodies specific to germ cell ALP may be conjugated to an appropriate toxin and used for site-directed therapy.

The peptide fragments having the following sequences are also provided:

NH$_2$-Lys-Asn-Leu-Ile-Met-Phe-Leu-Gly-COOH;
NH$_2$-Arg-Gly-Asn-Glu-Val-Ile-Ser-Val-Val-Asn-COOH;
NH$_2$-Arg-Thr-Glu-Leu-Leu-Gln-Ala-Ser-Leu-COOH; or
NH$_2$-Lys-Thr-Tyr-Ser-Val-Asp-COOH.

The following examples are intended to illustrate but not limit the invention. While they are typical of those that might be used, other alternative procedures known to those skilled in the art may be alternatively employed.

EXAMPLE I

Isolation and Purification of Germ Cell ALP

A sample of seminoma was obtained after surgical excision of the tumor from material remaining after pathological examination of an adult male. This testicular tumor sample was found to contain Nagao isozyme that displayed enzyme inhibition profiles and monoclonal antibody reactivities characteristic of the Type I PLAP-like enzyme (Millan et al. (1983) Eur. J. Biochem. 136:1, which is incorporated herein by reference).

The tissue was homogenized in 50 mM Tris pH 8.0 containing 0.1 mM phenylmethyl sulfanylfwonde (PMSF) (Byrl, Bethesda, Md.) and 0.05% Triton X-100 (Sigma, St. Louis, Mo.), extracted with n-butanol, heat inactivated for 10 minutes at 65° C., clarified by ultracentrifugation at 100.000 x G for 30 minutes and applied to a FPLC column (Pharmacia Fine Chemicals, Piscataway, N.J.). A single peak with ALP activity eluted at 0.2 M NaCl and was purified further on an H7 monoclonal antibody column as described in Millan et al. (1985) Int. J. Biochem 17:1033, which is incorporated herein by reference.

EXAMPLE II

Gene Sequence Analysis

Partial Mbo I digested human placental and spleenic DNA genomic libraries constructed in Charon 28 lambda phage were plated on *E. coli* C600 cells and screened by the method of Benton and Davis, (1977) Science 196:180, which is incorporated herein by reference. The probes used were either a 2.0 kb EcoRI-KpnI or a 261 bp EcoRI-BamHI fragment of the PLAP cDNA, identified as A in FIG. 1 from Millan (1986) J. Biol. Chem. 261:3112, which is incorporated herein by reference. The probes were radiolabelled with dCTP[$^{32}$P] using an oligolabelling kit (Pharmacia Fine Chemicals, Piscataway, N.J.). Positive clones were plaque purified and expanded as described in Maniatis et al., (1982) MOLECULAR CLONING: A LABORATORY MANUAL (Cold Spring Harbor Laboratory, Cold Spring Harbor, N.Y.), which is incorporated herein by reference. The DNA was analyzed by restriction enzyme mapping using BAM HI, PVM II and SMA 1 restriction endonucleases (Bethesda Research Laboratories, Bethesda, Md.).

Selected genomic fragments were subcloned into M13 mp18 and 19 or Bluescript M13 (Stratagene Cloning Systems, San Diego, Calif.) and sequenced using the universal 17-mer primer (P-L Biochemicals, Milwaukee, Wis.) and 17- and 18-mer oligonucleotides synthesized on an automated DNA Sequencer (Applied Biosystems, Foster City, Calif.), using the directions provided by the manufacturer. Sequencing of the clones was accomplished by the Sanger dideoxy-chain termination procedure (Sanger et al. (1977) Proc. Natl. Acad Sci. U.S.A. 74:5463), using the Klenow fragment of DNA polymerase and dATP[$^{35}$S] as a tracer. DNA sequences were assembled, analyzed and compared using the Microgenie sequence software (Beckman Instruments, Inc., Palo Alto, Calif.).

The DNA sequence was obtained for the Bam HI, Pvu II and Sma I fragments found to hybridize with the different subfragments of the PLAP cDNA. The complete nucleotide sequence of the germ cell ALP gene is presented in FIG. I. FIG. II shows the intron-exon structure and restriction enzyme map of the gene, as well as the sequencing strategy as indicated by the arrows. Open circles indicate priming by commercially available M13 or Bluescript primers. Open squares indicate priming by synthesized oligonucleotides, derived from the read DNA sequence as indicated in FIG. 2, and synthesized using an automated DNA synthesizer.

EXAMPLE III

Production of Germ Cell ALP specific antisera

The nonamer peptide NH$_2$-Lys-Leu-Gly-Pro-Glu-Thr-Phe-Leu-Ala-COOH was synthesized using an automated peptide synthesizer (Applied BioSystems, Foster City, Calif.) according to the instructions provided by the manufacturer. The peptide was coupled to keyhole limpet hemocyanin (KLH) (Sigma Chemical Co., St. Louis, Mo.) at a ratio of 4:1 (wt/wt) by the glutaraldehyde procedure of Avrameas, (1969) Immunochemistry 6:43, which is incorporated herein by reference. The same procedure was used for conjugating the peptide to bovine serum albumin (BSA). A New Zealand female rabbit was inoculated with 4 mg of the KLH conjugated peptide emulsified with complete Freund's adjuvant. Equivalent amounts of conjugated peptide in incomplete Freund's adjuvant were administered at 15 day intervals thereafter for a total of 6 administrations. Test bleedings were checked for antibody titer in sandwich ELISA using 15 μg/ml BSA-conjugated peptide for coating. Total IgG from positive bleedings was isolated on a protein A-Sepharose column (Pharmacia Fine Chemicals, Piscataway, N.J.). Coupling of the peptide to CNBr-activated Sepharose 4B (Pharmacia Fine Chemicals, Piscataway, N.J.) was accomplished according to the manufacturer's instructions to obtain 10 mg of peptide per ml sepharose. Subsequently, anti-peptide IgG was bound to the peptide-sepharose column in 50 mM Tris pH 8.0 containing 0.15 M NaCl (TBS), eluted with 0.1 M glycine/HCl buffer pH 2.s and neutralized with 10×TBS. The recovered antisera was found to bind to germ cell ALP.

EXAMPLE IV

Immunoassay for Germ Cell ALP

Samples of body fluid such as serum or a cellular extract suspected of containing germ cell ALP is obtained and utilized in an immunoenzymometric assay to detect the presence of germ cell ALP.

Monoperse polymer particles (MPP) Dynospheres $^R$X P4101, (Dyno Industries A/S, Oslo, Norway) is coupled to sheep antirabbit IgG (Ab$_2$) according to the method of Nustad, et al., Em. Surg. Res. 16 (Supp. 2):80 (1984). Antibodies produced by the method of Example III are incubated with the antibody bound particles overnight, with end-over-end rotation. The solid phase reagent thus prepared is extensively washed with pH 7.5 assay buffer, containing, per liter, 50 mmol of Tris, 0.15 mol of NaCl, 0.1 g of bovine serum albumin, 0.1 mL of Tween 20 (polyoxyethylene sorbitan monolaurate; (ICI Americas, Inc.), and 0.1 g of thimerosal. The reagent is then diluted so as to contain 0.2 µq antibody per 100 µL of particle suspension. Upon centrifugation, the particles form a firm pellet, approximately 1 µL in volume, which is readily dispersed upon addition of wash buffer or substrate.

Fifty µL samples are incubated with µL samples of the germ cell ALP specific antibody conjugated particles for 30 minutes in disposable polystyrene tubes. Two mL of assay buffer containing 0.5 mmol of MgCl and 10 mmol of p-nitrophenyL phosphate (Sigma Chemical Co., St. Louis, Mo.) and the solution centrifuged 10 minutes at 1500×g. The supernatant is decanted by inversion, and then pellet washed with 2 mL of assay buffer. 0.5 mL of buffered substrate solution is added to each tube, vortex-mixed and incubated in a water-bath at 37° C. for 3 hours. To stop the enzyme reaction, 0.5 mL of 40 mmol/L L-Phe in diethanolamine buffer is added to each tube. Vortex-mised again, centrifuged for 20 minutes at 2500×g. The solutions are 200 µL of the supernates is transferred to a 96-well microtitplates and the absorbance at 405 nm recorded (Titertek Multiskan spectrophotometer, Flow Laboratories, McLean, Va.).

The enzymatic activity of the antigen is used as the means of detection. The reaction rate is proportional to the amount of bound germ cell ALP, and can be quantified by comparison to standards.

Although the invention has been described with reference to the presently-preferred embodiment, it should be understood that various modifications can be made without departing from the spirit of the invention. Accordingly, the invention is limited only by the following claims.

I claim:

1. Human germ cell ALP having substantially the amino acid sequence presented in FIG. 1, said human germ cell ALP being completely free of contaminants associated with purification from a natural source.

2. The peptide fragment wherein the amino acid sequence of the peptide is NH$_2$-Lys-Leu-Gly-Pro-Glu--Thr-Phe-Leu-Ala-COOH.

3. The peptide fragment wherein the amino acid sequence of the peptide is
  a. NH$_2$-Lys-Asn-Leu-Ile-Met-Phe-Leu-Gly-COOH
  b. NH$_2$-Arg-Gly-Asn-Glu-Val-Ile-Ser-Val-Val-Asn-COOH
  c. NH$_2$-Arg-Thr-Glu-Leu-Leu-Gln-Ala-Ser-Leu-COOH or
  d. NH$_2$-Lys-Thr-Tyr-Ser-Val-Asp-COOH.

* * * * *